(12) United States Patent
Spratt et al.

(10) Patent No.: US 11,065,038 B2
(45) Date of Patent: Jul. 20, 2021

(54) FRACTURE REDUCTION USING IMPLANT BASED SOLUTION

(71) Applicant: Medos International Sarl, Le Locle (CH)

(72) Inventors: Frank Spratt, Middleboro, MA (US); Kevin Lee, Canton, MA (US); Albert Montello, Duxbury, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/984,600

(22) Filed: Aug. 4, 2020

(65) Prior Publication Data
US 2021/0038266 A1 Feb. 11, 2021

Related U.S. Application Data

(60) Provisional application No. 62/884,460, filed on Aug. 8, 2019.

(51) Int. Cl.
*A61B 17/70* (2006.01)

(52) U.S. Cl.
CPC ...... *A61B 17/7037* (2013.01); *A61B 17/7023* (2013.01); *A61B 17/7052* (2013.01)

(58) Field of Classification Search
CPC ........................................ A61B 17/7001–7052
See application file for complete search history.

(56) References Cited

U.S. PATENT DOCUMENTS

| 4,433,677 A | * | 2/1984 | Ulrich | A61B 17/7055 606/250 |
|---|---|---|---|---|
| 7,087,057 B2 | | 8/2006 | Konieczynski et al. | |
| 7,473,269 B1 | * | 1/2009 | Hynes | A61B 17/7011 606/250 |
| 7,618,443 B2 | | 11/2009 | Abdou | |
| 7,901,433 B2 | * | 3/2011 | Forton | A61B 17/7055 606/250 |
| 7,901,434 B2 | | 3/2011 | Drewry | |
| 7,909,852 B2 | * | 3/2011 | Boomer | A61B 17/7023 606/246 |
| RE44,392 E | * | 7/2013 | Hynes | A61B 17/7023 606/279 |
| 8,496,686 B2 | | 7/2013 | Berg et al. | |

(Continued)

FOREIGN PATENT DOCUMENTS

| WO | 2006/102443 A3 | 9/2006 |
|---|---|---|
| WO | 2017093863 A1 | 6/2017 |

*Primary Examiner* — Nicholas J Plionis
(74) *Attorney, Agent, or Firm* — Mintz Levin Cohn Ferris Glovsky and Popeo, P.C.

(57) ABSTRACT

Various angularly-adjustable spinal fixation systems are provided and generally include an articulating connector having first and second elongate rods extending therefrom, and first and second polyaxial bone screw assemblies configured to seat the first and second rods therein. The rods are configured to be seated within receiver heads of the polyaxial bone screw assemblies when the screws are implanted in opposed lateral sides of a vertebra, thereby allowing the receiver heads to be manipulated relative to the rods to reduce one or more posterior fractures. A joint on the articulating connector can also be manipulated to reduce one or more anterior fractures. The entire construct can be locked to maintain the fractures in the reduced configuration.

17 Claims, 12 Drawing Sheets

(56) References Cited

U.S. PATENT DOCUMENTS

| | | | |
|---|---|---|---|
| 8,657,856 B2 | 2/2014 | Gephart et al. | |
| 8,690,923 B2 | 4/2014 | Lynch | |
| 9,211,145 B2 | 12/2015 | Pereiro de Lamo et al. | |
| 9,393,052 B2 | 7/2016 | Berg et al. | |
| 9,439,690 B2* | 9/2016 | Mouw | A61F 2/44 |
| 9,532,811 B2 | 1/2017 | Black et al. | |
| 9,549,764 B2 | 1/2017 | Sutterlin, III | |
| 9,662,142 B2 | 5/2017 | Roberto et al. | |
| 9,668,772 B1 | 6/2017 | Crawford et al. | |
| 9,717,535 B2 | 8/2017 | Refai et al. | |
| 9,895,174 B2 | 2/2018 | Ozdil et al. | |
| 9,918,744 B2 | 3/2018 | Ritland | |
| 9,956,009 B1 | 5/2018 | Shoshtaev | |
| 9,956,084 B2 | 5/2018 | Larson et al. | |
| 9,974,572 B2 | 5/2018 | Boomer et al. | |
| 10,034,693 B2 | 7/2018 | Stern | |
| 10,034,694 B2 | 7/2018 | Mouw | |
| 2004/0147928 A1 | 7/2004 | Landry et al. | |
| 2004/0172024 A1 | 9/2004 | Gorek | |
| 2006/0229611 A1 | 10/2006 | Avery et al. | |
| 2007/0088358 A1 | 4/2007 | Yuan et al. | |
| 2009/0093847 A1* | 4/2009 | Wilcox | A61B 17/705 606/259 |
| 2011/0098748 A1* | 4/2011 | Jangra | A61B 17/7013 606/278 |
| 2013/0204302 A1* | 8/2013 | Rezach | A61B 17/7049 606/260 |
| 2013/0274807 A1* | 10/2013 | Prajapati | A61B 17/7049 606/278 |
| 2014/0058450 A1* | 2/2014 | Arlet | A61B 17/7013 606/256 |
| 2014/0066990 A1* | 3/2014 | Akbarnia | A61B 17/705 606/278 |
| 2017/0311986 A1* | 11/2017 | McNab | A61B 17/708 |
| 2017/0319238 A1 | 11/2017 | Boehm, Jr. | |

* cited by examiner

FRACTURE REDUCTION USING IMPLANT BASED SOLUTION

CROSS-REFERENCE TO RELATED APPLICATIONS

The present application claims priority to U.S. Provisional Application 62/884,460 filed Aug. 8, 2019, entitled "Fracture Reduction Using Implant Based Solution," which is hereby incorporated by reference herein in its entirety.

FIELD

Systems and methods for reduction of anterior and posterior vertebral fractures.

BACKGROUND

Current surgical techniques for reducing and stabilizing anterior and posterior vertebral fractures involve the use of monoaxial screws implanted into the lateral masses of a vertebra and linked together via rods. During the current reduction and stabilization process, a surgeon implants the monoaxial screws, installs the rods, and bends the rods while reducing the posterior fracture via application of compression. This technique is difficult for the surgeon to perform, and presents challenges for stabilization, as tightening of both monoaxial screws and reduction of the fracture must occur simultaneously. In addition, the orientation of the monoaxial screw head and the contour of the rod is critical in closing the fractures. Furthermore, the surgeon must perform this in one shot, leaving very limited opportunity for adjustments or corrective measures, and it may not always result in optimal closure of both the anterior and posterior fractures.

SUMMARY

In one aspect, a method for reducing and stabilizing fractures in a vertebra is described. An exemplary method can include implanting a first bone screw into a first lateral side of the vertebra, and implanting a second bone screw into a second, opposite lateral side of the vertebra. The method can further include positioning a first rod within a first receiver head coupled to the first bone screw and positioning a second rod within a second receiver head coupled to the second bone screw. The first receiver head and the second receiver head can be manipulated relative to the first rod and the second rod, and relative to an articulating joint coupling the first rod and the second rod together to thereby move at least one fracture formed in the vertebra into a reduced position. In some embodiments, the first receiver head and the second receiver head can be polyaxially coupled to the first bone screw and the second bone screw, respectively, such that the first receiver head and the second receiver head pivot relative to the first bone screw and the second bone screw, respectively, during at least one of positioning the first rod and the second rod within the first receiver head and the second receiver head respectively, and manipulating the first receiver head and the second receiver head.

In some embodiments, the at least one fracture can include at least one posterior fracture in the vertebra and at least one anterior fracture in the vertebra. Manipulating the first receiver head and the second receiver head can move the at least one posterior fracture into a reduced position, and manipulating the first rod and the second rod can move the at least one anterior fracture into a reduced position. In such an embodiment, the first receiver head and the second receiver head can be manipulated prior to manipulating the first rod and the second rod. In other embodiments, manipulating the first receiver head and the second receiver head relative to the first rod and the second rod can include slidably moving the first receiver head and the second receiver head along the first rod and the second rod. In yet other embodiments, manipulating the first rod and the second rod relative to the articulating joint can include pivoting the first rod and the second rod about the articulating joint to adjust an angle between the first rod and the second rod.

The method can further include locking the first receiver head and the second receiver head to the first rod and the second rod, and locking the articulating joint to thereby prevent movement of the first receiver head, the second receiver head, the first rod, and the second rod, thereby maintaining the at least one fracture in the reduced position. In some embodiments, the first receiver head and the second receiver head can be locked to the first rod and the second rod, respectively, prior to locking the articulating joint.

In some embodiments, the method can include coupling each of the first rod and the second rod to at least one additional receiver head of at least one additional bone screw implanted in at least one additional vertebra. In such an embodiment, each of the first rod and the second rod can include proximal portions that can be seated within the first receiver head and the second receiver head respectively, and distal portions that extend at an angle relative to the proximal portions, respectively, and that are seated in the at least one additional receiver head. In certain exemplary embodiments, the proximal portions of the first rod and the second rod can extend in a medial-lateral direction relative to the vertebra, and the distal portions of the first rod and the second rod can extend in a craneal-caudal direction relative to the vertebra.

In another aspect, a method for reducing and stabilizing features in a vertebra is provided and includes implanting a first bone screw into a first lateral side of a vertebra and a second bone screw into a second, opposite lateral side of the vertebra. The method can further include manipulating the first receiver head and the second receiver head relative to the first rod and the second rod and manipulating the first rod and the second rod relative to an articulating joint coupling the first rod and the second rod together to thereby move at least one fracture formed in the vertebra into a reduced position. In some embodiments, the first receiver head and the second receiver head can be polyaxially coupled to the first bone screw and the second bone screw, respectively, such that the first receiver head and the second receiver head pivot relative to the first bone screw and the second bone screw, respectively, during at least one of positioning the first rod and the second rod within the first receiver head and the second receiver head respectively, and manipulating the first receiver head and the second receiver head.

In some embodiments, the at least one fracture can include at least one posterior fracture in the vertebra and at least one anterior fracture in the vertebra. In such embodiments, manipulating the first receiver head and the second receiver head can move the at least one posterior fracture into a reduced position, and manipulating the first rod and the second rod can move the at least one anterior fracture into a reduced position. In such an embodiment, the first receiver head and the second receiver head can be manipulated prior to manipulating the first rod and the second rod. In other embodiments, manipulating the first receiver head and the second receiver head relative to the first rod and the second rod can include slidably moving the first receiver head and the second receiver head along the first rod and the second rod. In yet other embodiments, manipulating the first rod and the second rod relative to the articulating joint can include pivoting the first rod and the second rod about the articulating joint to adjust an angle between the first rod and the second rod.

The method can further include locking the first receiver head and the second receiver head to the first rod and the second rod, and locking the articulating joint to thereby prevent movement of the first receiver head, the second receiver head, the first rod, and the second rod, thereby maintaining the at least one fracture in the reduced position. In some embodiments, the first receiver head and the second receiver head can be locked to the first rod and the second rod, respectively, prior to locking the articulating joint.

In some embodiments, the method can include coupling each of the first rod and the second rod to at least one additional receiver head of at least one additional bone screw implanted in at least one additional vertebra. In such an embodiment, each of the first rod and the second rod can include proximal portions that can be seated within the first receiver head and the second receiver head, respectively, and distal portions that can extend at an angle relative to the proximal portions respectively, and can be seated in the at least one additional receiver head. In certain exemplary embodiments, the proximal portions of the first rod and the second rod can extend in a medial-lateral direction relative to the vertebra, and the distal portions of the first rod and the second rod can extend in a craneal-caudal direction relative to the vertebra.

In another aspect, a system for reducing and stabilizing fractures is provided and includes a first bone screw assembly, a second bone screw assembly, and an articulating connector. The first bone screw assembly can include a first bone screw with a shank having a head on a proximal end thereof, and a first receiver having the head of the first bone screw being polyaxially seated therein. The second bone screw assembly can include a second bone screw with a shank having a head on a proximal end thereof, and a second receiver having the head of the second bone screw being polyaxially seated therein. The articulating connector can include first and second elongate rods, each having a proximal end coupled to an articulation joint allowing the first and second elongate rods to pivot about the articulation joint to adjust an angle therebetween. The articulation joint can include a locking mechanism configured to lock the first and second elongate rods at a fixed angular orientation relative to one another. The first rod can have a length configured to allow the first rod to be seated within the first receiver of the first bone screw assembly when the first bone screw assembly is implanted in a lamina on a first lateral side of a first vertebra, and the second rod can have a length configured to allow the second rod to be seated within the second receiver of the second bone screw assembly when the second bone screw assembly is implanted in a lamina on a second lateral side of the first vertebra, opposite the first lateral side, such that the articulation joint is located along a medial portion of the first vertebra.

In some embodiments, the first rod can include proximal and distal portions. The proximal portion of the first rod can extend from the articulation joint and it can be configured to extend to and be seated within the first receiver when the first bone screw assembly is implanted in a lamina on the first lateral side of the first vertebra, and the distal portion of the first rod can extend transverse to the proximal portion of the first rod such that the distal portion can be configured to be seated within a receiver of a bone screw implanted in a lamina on a first lateral side of a vertebra adjacent the first vertebra. The second rod can also include proximal and distal portions. The proximal portion of the second rod can extend from the articulation joint and can be configured to extend to and be seated within the second receiver when the second bone screw assembly is implanted in a lamina on the second lateral side of the first vertebra, and the distal portion of the second rod can extend transverse to the proximal portion of the second rod such that the distal portion can be configured to be seated within a receiver of a bone screw implanted in a lamina on a second lateral side of the vertebra adjacent the first vertebra. In certain exemplary embodiments, the first and second portions of each of the first and second rods can extend substantially perpendicular to one another.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are nonlimiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various angularly-adjustable spinal fixation systems and methods are provided for reducing one or more vertebral fractures. In general, the system includes an articulating connector having first and second elongate rods extending therefrom, and first and second polyaxial bone screw assemblies configured to seat the first and second rods therein. The rods are configured to be seated within receiver heads of the polyaxial bone screw assemblies when the screws are implanted in opposed lateral sides of a vertebra, thereby allowing the receiver heads to be manipulated relative to the rods to reduce one or more posterior fractures. A joint on the articulating connector can also be manipulated to reduce one or more anterior fractures. The entire construct can be locked to maintain the fractures in the reduced configuration. By this method, the surgeon can use the rods, screws, and articulating joint to fully reduce and stabilize anterior and/or posterior fractures.

Angularly-Adjustable Spinal Fixation Device

Figure 1A:
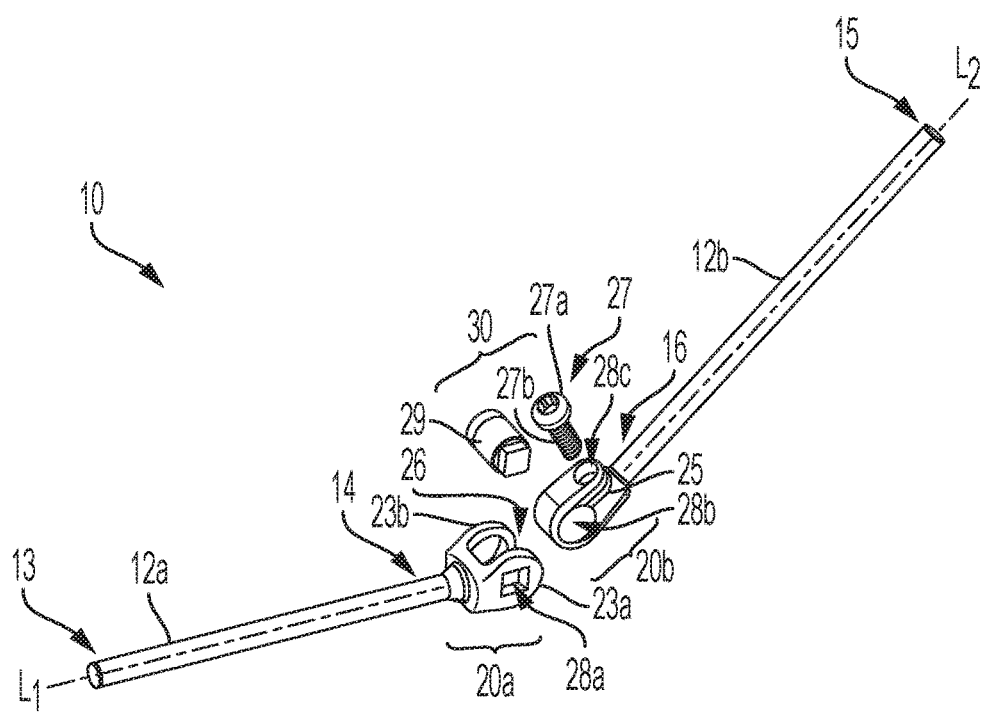
FIG. 1A is an exploded view of one embodiment of an adjustable-angle spinal fixation device having male and female connecting features.
Figure 1B:
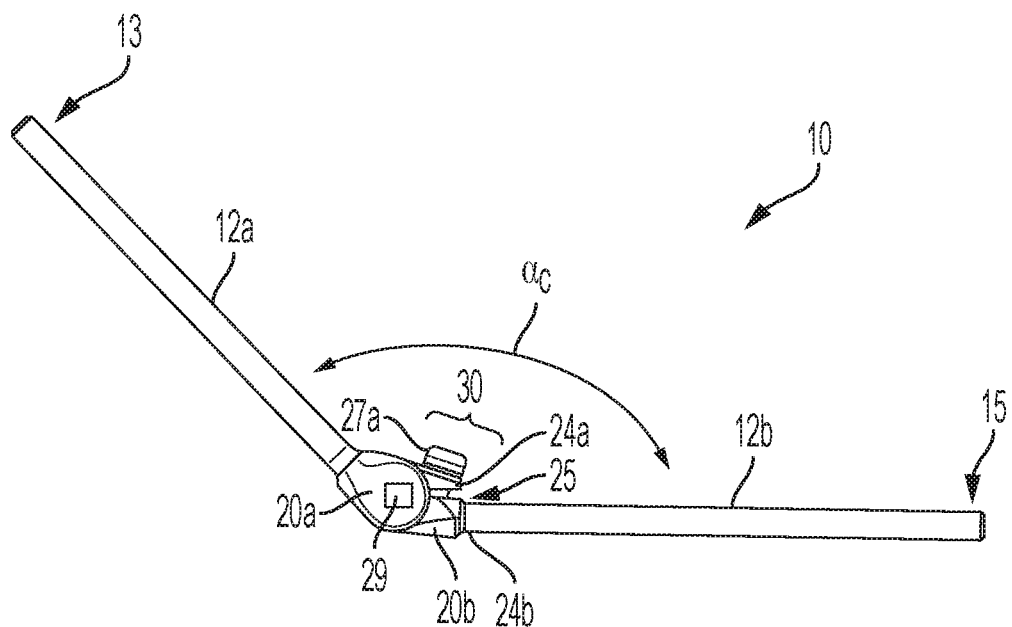
FIG. 1B is a side, assembled view of the adjustable-angle spinal fixation device of in FIG. 1A shown in a locked position.

FIGS. 1A-1B illustrate one exemplary embodiment of an angularly-adjustable spinal fixation device 10 having first and second elongate rods 12a, 12b, an articulating joint 20 including a female connector 20a and a male connector 20b formed on proximal ends 14, 16 of each of the first and second elongate rods 12a, 12b, respectively, and a locking mechanism 30 that is adapted to lock the first and second elongate rods 12a, 12b in a fixed position relative to one another. Such an exemplary angularly-adjustable spinal fixation device is described in U.S. Pat. No. 7,909,852, which is hereby incorporated by reference in its entirety. In use, the first and second elongate rods 12a, 12b can be angularly adjusted relative to one another and, once properly positioned, they can be locked in a fixed position relative to one another using the locking mechanism 30.

The first and second elongate rods 12a, 12b can each have any shape or size, and each elongate rod 12a, 12b can vary in diameter relative to one another. The elongate rods 12a, 12b can also vary in length depending on the intended use. For example, each of the elongate rods 12a, 12b can have a length configured to allow the rods to be seated in a bone screw, an example of which is described in further detail below, when the bone screw is implanted in a lamina of a vertebra. In the illustrated embodiment, the first and second elongate rods 12a, 12b are substantially cylindrical spinal rods, each having a distal portion 13, 15 that is adapted to mate to a spinal anchor, such as a hook, screw, bolt, plate, etc. As indicated above, the proximal ends 14, 16 of each elongate rod 12a, 12b includes the connecting features 20a, 20b formed thereon.

Figure 1C:
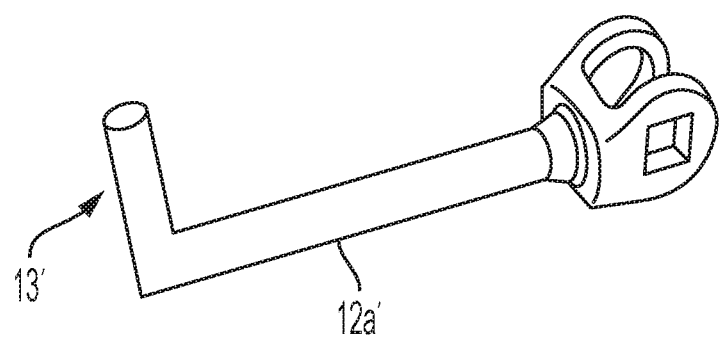
FIG. 1C is a perspective view of another embodiment of a portion of an adjustable-angle spinal fixation device having a spinal rod with a distal portion that extends at an angle away from a longitudinal axis of a proximal portion of the spinal rod.

While the illustrated rods are linear, the distal portions 13, 15 can extend at an angle relative to the elongate rods 12a, 12b. FIG. 1C, the distal portion 13' of one of the elongate members, e.g., the first elongate rod 12a', can extend at an angle relative to the longitudinal axis of the first elongate rod 12a'.

Continuing to refer to FIGS. 1A-1B, the connecting features 20a, 20b can have a variety of configurations, but they should be adapted to allow for angular adjustability of the first and second elongate rods 12a, 12b relative to one another. In the embodiment shown in FIGS. 1A-1B, the connecting feature 20a on the first elongate rod 12a is in the form of a female connector, and the connecting feature 20b on the second elongate rod 12b is in the form of a male connector.

While the connectors 20a, 20b can have a variety of configurations, in an exemplary embodiment the female connector 20a has opposed arms 23a, 23b that are spaced a distance apart from one another to form an open recess 26 therebetween for seating the male connector 20b. The male connector 20b can vary in shape and size, but it preferably has a shape and size configured to be received within the female connector 22.

Figure 1D:
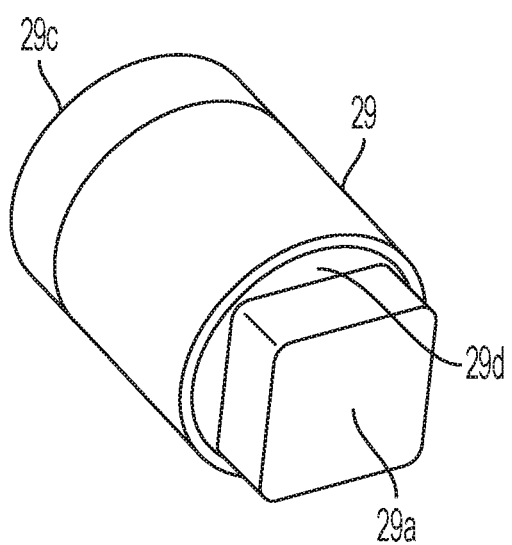
FIG. 1D is a perspective view of a central mating element of the adjustable-angle spinal fixation device of FIG. 1A.

Each connector 20a, 20b also preferably includes a central bore 28a, 28b that extends therethrough in a direction that is substantially perpendicular to a longitudinal axis $L_1$, $L_2$ of each of the first and second elongate rods 12a, 12b. The central bore 28a, 28b is adapted to receive a central mating element 29 therethrough for mating the connectors 20a, 20b, and for allowing one or both connectors 20a, 20b to rotate thereabout. The central mating element 29 can have a variety of configurations, however FIG. 1D illustrates a central mating element 29 having a substantially cylindrical shape and including proximal and distal ends 29c, 29d. In a preferred embodiment, one of the connectors, e.g., the female connector 20a, is configured to receive the mating element 29 such that the female connector 20a and the mating element 29 are in a fixed position relative to one another, and the male connector 20b is free to rotate about the mating element 29 and relative to the female connector 20a. This can be achieved, for example, by providing complementary features on the mating element 29 and the female connector 20a to prevent rotation relative to one another. As shown in FIGS. 1A-1B, the portion of the bore 28a that extends through the first arm 23a has a substantially square shape, and the distal end 29d of the central mating element 29 includes a substantially square-shaped protrusion 29a formed thereon and adapted to be disposed within the corresponding bore 28a formed in the female connector 20a. As a result, when the device 10 is in use, the female connector 20a is locked in a fixed position relative to the mating element 29, but the male connector 20b is free to rotate thereabout. A person skilled in the art will appreciate that the complementary features on the mating element 29 and the female connector 20a can have a variety of other configurations and by way of nonlimiting example, the complementary mating features can have a hexagonal shape, an octagonal shape, a D-shape, or any other shape that prevents rotation of the female connector 20a relative to the mating element 29.

As previously stated, the device 10 also includes a locking mechanism 30 that is adapted to lock the first and second elongate rods 12a, 12b in a fixed position relative to one another. While virtually any technique can be used to lock the elongate rods 12a, 12b in a fixed position, FIGS. 1A-1B illustrate an exemplary embodiment of a locking mechanism 30. In this embodiment, the male connector 20b is in the form of a clamp mechanism and more particularly it includes a slot 25 extending therethrough and in communication with the central bore 28 formed therein, as shown in more detail in FIG. 1A. The slot 25 separates the male connector 20b into upper and lower portions 24a, 24b that are movable between an open position and a closed position in which the male connector 20b is adapted to engage the mating element 29 extending through the central bore 28b.

In order to move the upper and lower portions 24a, 24b to the closed position, the male connector 20b can include a receiving bore 28c formed therein and extending through the upper and lower portions 24a, 24b. The receiving bore 28c is adapted to receive a fastening element 27 that is effective to pull one or both of the upper and lower portions 24a, 24b toward one another to close the slot 25. As a result, the central bore 28b extending through the male connector 20b is decreased in size, thereby allowing the male connector 20b to engage the mating element 29 and preventing rotation of the second elongate rod 12b relative to the first elongate rod 12a.

The fastening element 27 that is disposed through the receiving bore 28c can have a variety of configurations, and it can be, for example, a screw, anchor, or bolt. In the illustrated embodiment, as shown in FIG. 1A, the fastening element 27 is a threaded member, e.g., a screw, having a head 27a and a thread shank 27b. The receiving bore 28c formed in the male connector 20b can thus include threads formed therein for mating with the threaded shank 27b on the fastening element 27. More preferably, however, the portion of the receiving bore 28c formed in the upper portion 24a of the male connector 20b is non-threaded to allow free rotation of the threaded member 27 with respect thereto, and the portion of the receiving bore 28c formed in the lower portion 24b of the male connector 20b is threaded to mate with the threaded shank 27b. This allows the fastening element 27 to pull the upper portion 24a toward the lower portion 24b, thereby locking the portions 24a, 24b relative to one another and locking the male connector 20b relative to the mating element 29.

In use, the fastening element 27 can be partially threaded into the bore 28c formed in the male connector 20b to allow the first and second elongate rods 12a, 12b to rotate relative to one another. Although the elongate rods 12a, 12b can be adapted for multi-axial rotation, in the illustrated embodiment the elongate rods 12a, 12b rotate along a single plane. Each elongate rod 12a, 12b may be configured to rotate such that a complementary angle $\alpha_c$ between the elongate rods 12a, 12b, as shown in FIG. 1B, can range from about 0° to 135° in each direction from a coaxial position, and more preferably from about 60° to 135° in each direction from a coaxial position. Once the elongate rods 12a, 12b are in a desired position relative to one another, the fastening element 27 can be fully threaded into the bore 28c in the male connector 20b to cause the male connector 20b to engage the mating element 29, thereby preventing rotation of the second elongate rod 12b relative to the first elongate rod 12a.

Polyaxial Bone Screw

Figure 2:
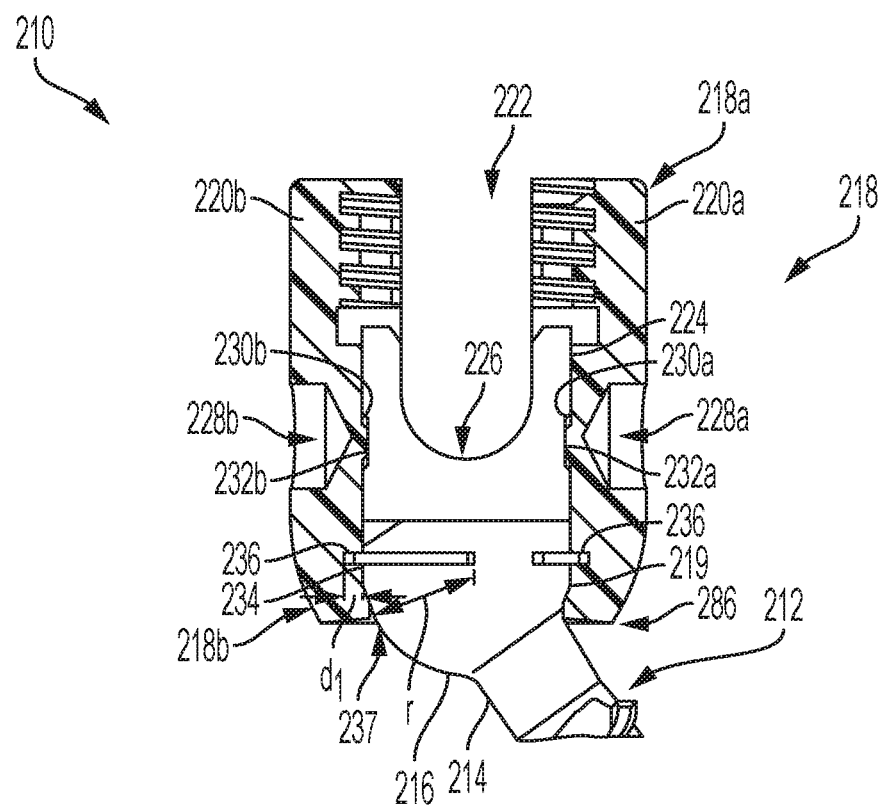
FIG. 2 is an enlarged, partially cross-sectional view of one embodiment of a polyaxial bone screw assembly.

FIG. 2 illustrates one embodiment of a polyaxial bone screw assembly 210 that can be used with the methods and devices herein. Such an exemplary polyaxial bone screw assembly is described in U.S. Pat. No. 7,087,057, which is hereby incorporated by reference in its entirety. As shown, the polyaxial bone screw assembly includes a receiver head 218 having a snap ring 234 and a compression cap 224 therein. The receiver head 218 is generally U-shaped and includes opposed side walls or legs 220a, 220b that are substantially parallel to one another and that define a rod-receiving portion 222 for seating a spinal fixation rod. A distal end 218b of the receiver head 218 includes an axial opening (not shown) formed therein and having a diameter sized to permit passage of a shank 214 of the bone screw 212 therethrough while maintaining the spherical head 216 therein. The receiver head 218 further includes a spherical seat 219 adjacent to the distal opening for polyaxially seating the spherical head 216 of the bone screw 212.

The compression cap 224 has a generally cylindrical shape and includes a rod-receiving proximal surface 226, and a concave distal surface (not shown) that is adapted to fit around and seat a portion of the spherical head 216 of the bone screw 212. The snap ring 234 can be adapted to expand to fit around at least a portion of the spherical head 216. While the snap ring 234 is shown having a C-shape, the snap ring can 234 can have a variety of other configurations. In use, it is adapted to fit within a corresponding groove 236 formed around an inner surface of the receiver head 218. The groove 236 maintains the snap ring 234 at a particular location with respect to the spherical head 216 of the bone screw such that the snap ring 234 frictionally engages the head 216. One skilled in the art will appreciate that a variety of other techniques and fastening members are known for use in retaining the spherical head 216 (and any rod) within the receiver head 218.

Still referring to FIG. 2, the bone screw assembly 210 can be assembled by first placing the snap ring 234 within the groove 236 in the receiver head 218. The threaded shank 214 of the screw 212 can then be inserted from a proximal end through the axial opening 237 formed in the distal end 218b of the receiver head 218. The snap ring 234 can frictionally engage the spherical head 216 when the head is seated in the spherical seat 219. The compression cap 224 can then be placed in the receiver head 218 and can be positioned just proximal of the head 216. To prevent the compression cap 224 from popping out of the receiver head 218, a tool can be inserted into each of the opposed bores 228a, 228b to deform a deformable material 232a, 232b, which extends across the inner surface of the receiver head 218, into corresponding detents 230a, 230b formed in the compression cap 224. As a result, the compression cap 224 is prevented from moving in a proximal direction, thereby preventing the spherical head 216 from moving proximally and becoming disengaged with the snap ring 234. One skilled in the art will appreciate that a variety of other techniques and fastening members are known for use in retaining the spherical head 216 (and any rod) within the receiver head 218.

The frictional forces created by the snap ring 234 that act on the spherical head 216 of the screw 212 will allow the screw 212 to be set at a desired angular orientation with respect to the receiver head 218, as shown in FIG. 2. The frictional forces can simply be overcome by grasping and moving the receiver head 218 with respect to the bone screw 212 to change the angular orientation. In other words, a force greater than the frictional engagement force is required to change the angular orientation of the bone screw 212 with respect to the receiver head 218. When it is desired to lock the construct, a set screw assembly can be threaded into the receiver head 218. An outer set screw can be threaded distally into engagement with the compression cap to apply a distal force to the compression cap 224, thereby engaging and locking the spherical head in a fixed position relative to the receiver head. As a result, the angular orientation of the bone screw 212 will be fixed. An inner set screw can be threaded distally into engagement with the rod to prevent moving of the receiver head along the rod. In other embodiments, a single set screw can both lock the rod and lock the angular orientation of the screw.

Handheld Manipulation Tool

Figure 3:
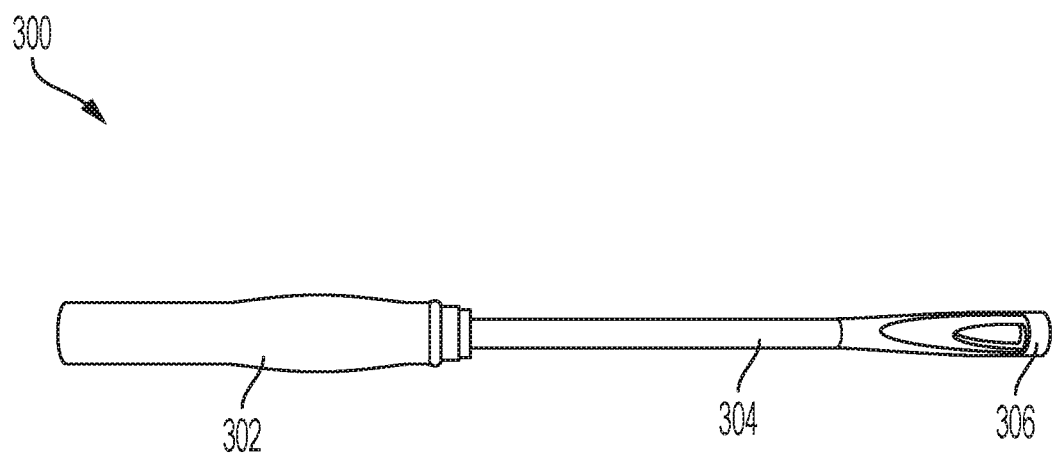
FIG. 3 is a side view of an embodiment of a handheld manipulation tool for use with a bone screw assembly and adjustable angle spinal fixation device.

FIG. 3 illustrates an embodiment of an exemplary handheld manipulation tool 300 for use in manipulating the position of the system components described above. The illustrated handheld manipulation tool 300 includes a proximal handle portion 302 configured to permit a user to grasp the tool 300, and a distal portion 304 configured to contact a bone screw assembly. The distal portion 304 can include a distal-most recess feature 306 configured to engage and adjust a position of a bone screw assembly. In particular, the feature 306 can be sized to receive a receiver of a bone screw assembly for manipulating the receiver relative to a spinal tool. A variety of other tools can be used to manipulate the bone screw assemblies and/or the elongate rods, including, without limitation, a rod clamp, a hand held rod bender, bending irons, and a counter torque device. Other tools known in the art for manipulation of bone screw assembles and/or elongate rods may be used.

Method for Reducing and Stabilizing Fractures

Figure 4A:
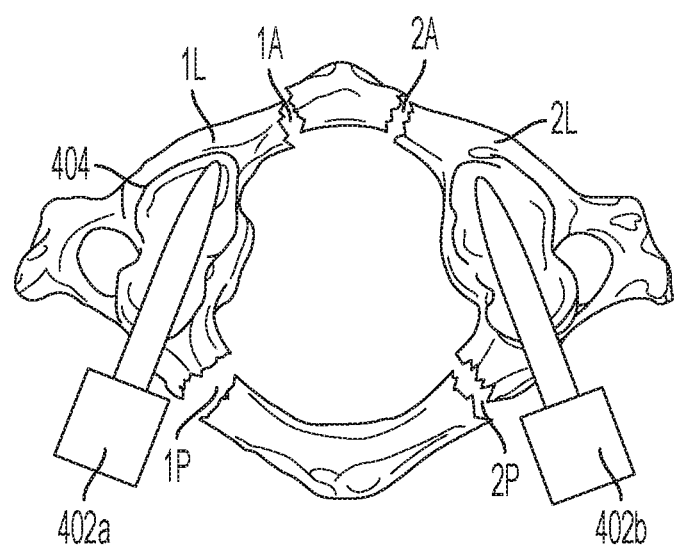
FIG. 4A is a top view of a fractured cervical vertebra with first and second bone screw assemblies implanted into lateral portions of the vertebra.

FIGS. 4A-4F illustrate one exemplary method for reducing and stabilizing fractures in a vertebra. While the method is discussed in connection with the angularly-adjustable spinal fixation device 10 of FIGS. 1A-1D, bone screw assembly 210 of FIG. 2, and handheld manipulation tool 300 of FIG. 3, the method can be performed using any components and tools having the same or similar features and characteristics. Furthermore, the method is discussed with respect to burst fractures of the C1 vertebra. Burst fractures of the C1 vertebra primarily occur when the occipital condyles of the skull are forced into the lateral masses of the C1 vertebra. Patients usually do not have a spinal cord injury or neurologic deficits because the fracture tends to spread bone fragments radially outward, away from the spinal cord. However, the vertebral arteries are at high risk of injury from the fragments, which can result in complications for the patient. FIG. 4A shows an illustration of a C1 vertebra 404 with a burst fracture, including first and second anterior fractures 1A and 2A of the anterior arch, and first and second posterior fractures 1P and 2P of the posterior arch. Although the method is discussed with respect, to burst fractures of the C1 vertebra, the method can also be used with respect to other types of vertebral fractures on any vertebra.

Figure 4B:
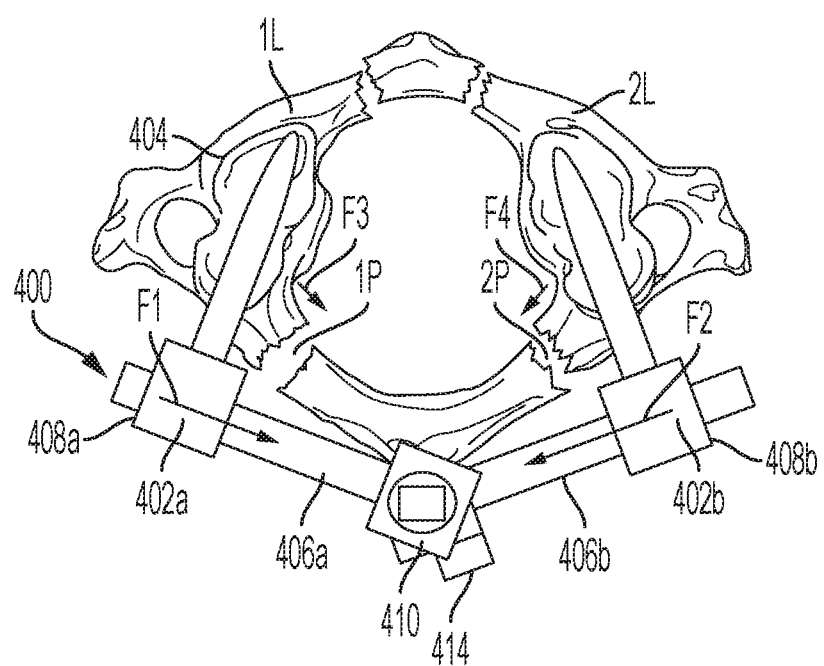
FIG. 4B is a top view of the fractured cervical vertebra of FIG. 4A with an adjustable angle spinal fixation device inserted into receiver heads of first and second bone screw assemblies.

In such a method, in preparation for installation of an angularly adjustable spinal fixation device 400, first and second bone screw assemblies 402a, 402b are implanted into opposed posterior lateral masses 1L and 2L of the fractured vertebra 404, as shown in FIG. 4A. The first and second elongate rods 406a, 406b of an angularly-adjustable spinal fixation device 400 can be manipulated and positioned within the first and second receiver heads 408a, 408b coupled to the first and second bone screw assemblies 402a, 402b, as shown in FIG. 4B. As shown, the articulating joint 410 is aligned with the midline of the spine, with the first and/or elongate rods 406a, 406b extending laterally away from the midline of the spine. In some embodiments, where posterior and/or anterior fractures are only present on one lateral side of the vertebra 404, the hinge can be positioned between the first and second bone screws 402a, 402b, but closer to the lateral side of the vertebra that is fractured. In yet other embodiments, either the first and/or second elongate rods 406a, 406b can be positioned through the head of at least one additional screw implanted in at least one additional vertebra adjacent to the fractured vertebra. In such an embodiment, angled rods as shown in FIG. 1C can be used.

Once the first and second elongate rods 406a, 406b are positioned within the first and second receiver heads 408a, 408b, the posterior fracture sites 1P and 2P can be compressed to reduce the posterior fractures. To reduce the posterior fractures, a tool, such as tool 300, can be placed on each of the first and second receiver heads 408a, 408b and manipulated to slide the heads along the corresponding elongate rods 406a, 406b until the fractures are in the desired, reduced position. Full reduction can be achieved, for example, by moving implanted bone screw 402a along elongate rod 406a in the direction of arrow F1, and moving implanted bone screw 402b along elongate rod 406b in the directions of arrow F2, as shown in FIG. 4B. By doing so, the first and second lateral masses 1L, 2L of the vertebra correspondingly move in the direction of arrows F3 and F4, respectively, thereby reducing the posterior fractures 1P and 2P. During the reduction, in some implementations, the angle of the each of the first and second receiver heads 408a, 408b can change with respect to the shanks of the first and second bone screws 402a, 402b to ensure the elongate rod and receiver head repositioning that occurs during compression can achieve full reduction of the posterior fractures. In some implementations, the tool can be placed on the first and second elongate rods to manipulate the rods and thereby reduce the posterior fractures.

Figure 4C:
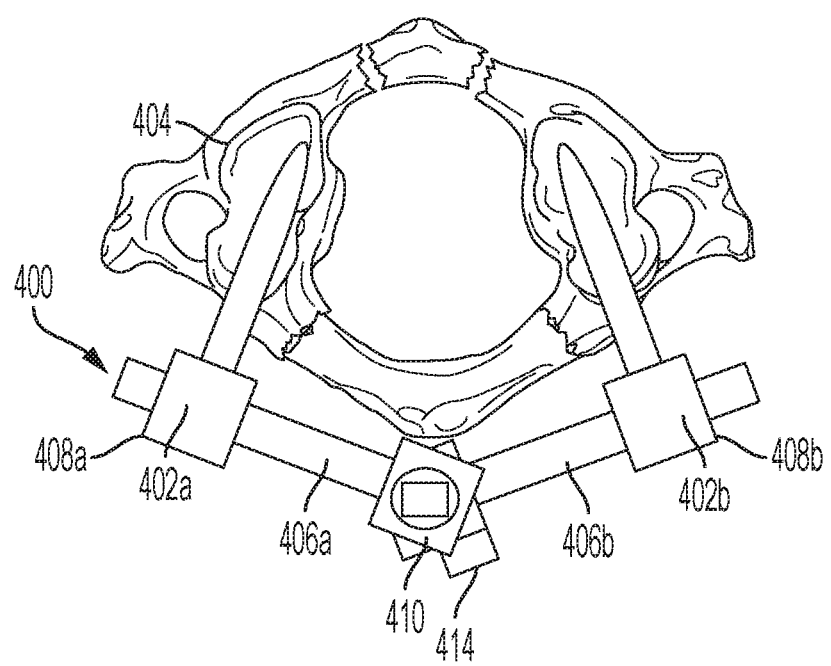
FIG. 4C is a top view of the fractured cervical vertebra of FIG. 4A with the posterior fracture reduced after compression and the rods locked to the screws to maintain the reduced posterior fracture.
Figure 4D:
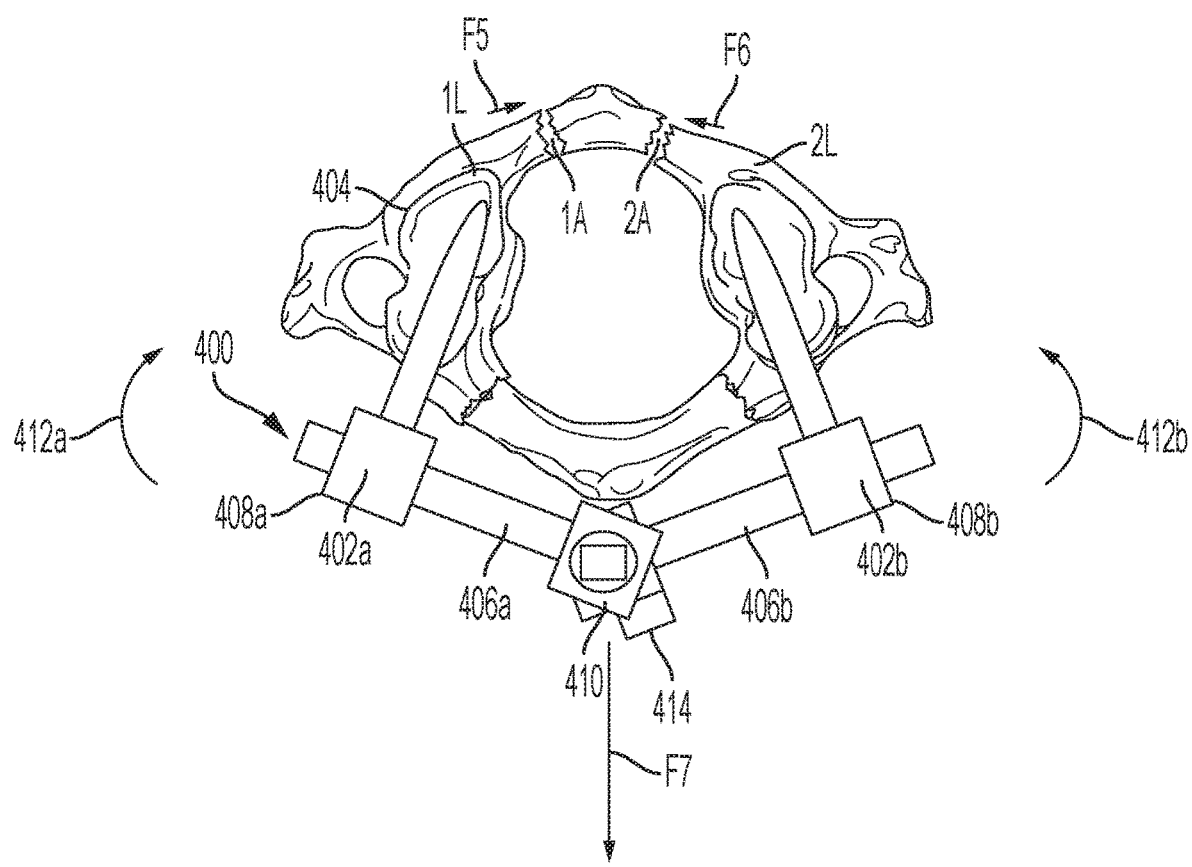
FIG. 4D is a top view of the fractured cervical vertebra of FIG. 4A with schematics demonstrating the forces applied to reduce the anterior fracture.

FIG. 4C shows the implanted system as positioned after the compression and reduction of the posterior fractures 1P and 2P have occurred. In some embodiments, where portions of the first and/or second elongate rods 406a, 406b extend outward of the first and second receiver heads 408a, 408b, the portions can be deformed and oriented proximally toward the occipital bone to maintain clearance with neighboring vertebrae. In other embodiments, the portions can be pre-positioned toward the occipital bone when the first and second elongate rods 406a, 406b are inserted into the first and second receiver heads 408a, 408b, obviating the need for manipulation.

Once the posterior fracture site(s) are reduced, the first and second receiver heads 408a, 408b can be locked, which can fix the orientation of the first and second receiver heads 408a with respect to the orientation of the shank of the bone screw assembly, and the position of the first and second receiver heads 408a, 408b within the first and second elongate rods 406a, 406b. Locking the first and second receiver heads 408a, 408b also has the effect of fixing the posterior position of the fractured vertebra and thereby stabilizing the compressed posterior fracture.

After the posterior fracture is stabilized, a pivot force can be applied to the first and second elongate rods 406a, 406b by use of a manipulation tool, such as a grasper, clamp, or rod bender. For example, applying a pivot force in the direction of arrow F7 can cause the first and second elongate rods 406a, 406b, and correspondingly the first and second bone screw assemblies 402a, 402b and the lateral masses 1L, 2L of the vertebra, to pivot about the articulating joint 410, thereby reducing the anterior fractures 1A and 2A in the direction of arrows F5 and F6. Since the bone screws 402a, 402b are locked in a fixed angular orientation and are locked in a fixed position on the first and second elongate rods 406a, 406b, pivotal movement of the joint will cause the first and second elongate rods 406a, 406b, the bone screws 402a, 402b, and lateral masses 1L, 2L to move as a unit. Such movement will thus cause the anterior portion of each of the lateral masses 1L, 2L to move inward, thereby reducing the fractures.

Figure 4E:
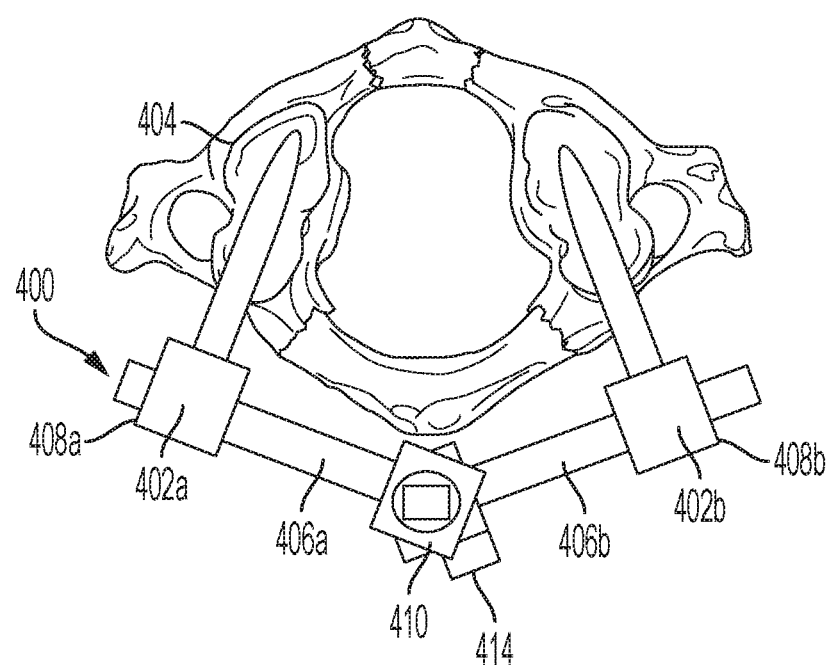
FIG. 4E is a top view of the cervical vertebra of FIG. 4A with the adjustable-angle spinal fixation device fully locked to maintain the anterior and posterior fractures in the reduced positions.

FIG. 4E shows the position of the vertebra after the pivoting force has been applied and the lateral masses 1L, 2L have moved in the direction of arrows F5 and F6. Once the anterior fractures have been reduced, the locking mechanism 414 on the hinge can be tightened to lock and maintain the angle between first elongate rod 406a and second elongate rod 406b. At this point, the vertebra is fully stabilized, and the fractures are reduced.

Figure 4F:
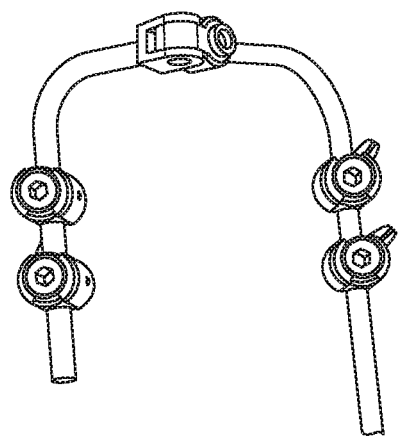
FIG. 4F is a perspective view of an adjustable angle spinal fixation device with elongate rods that are pre-bent.

The method detailed above has been described in the context of reducing and stabilizing vertebral fractures in a single vertebra. In some implementations, multi-level fixation can be achieved through the use of elongate rods that are pre-bent prior to implantation in order to capture bone screws longitudinally implanted along adjacent vertebral levels. An example of an angularly-adjustable spinal fixation device that includes pre-bent elongate rods is shown in FIG. 4F.

In the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A method for reducing and stabilizing fractures in a vertebra, comprising:
   positioning first and second rods within first and second receiver heads coupled to first and second bone screws implanted on opposed lateral sides of a vertebra;
   manipulating the first and second receiver heads relative to the first and second rods and manipulating the first and second rods relative to an articulating joint coupling the first and second rods to thereby move at least one fracture formed in the vertebra into a reduced position; and
   locking the first and second receiver heads to the first and second rods, and locking the articulating joint formed between the first and second rods to thereby prevent movement of the first and second receiver heads and the first and second rods, thereby maintaining the at least one fracture in the reduced position.

2. The method of claim 1, wherein the at least one fracture comprises at least one posterior fracture in the vertebra and at least one anterior fracture in the vertebra, and manipulating the first and second receiver heads moves the at least one posterior fracture into a reduced position and manipulating the first and second rods moves the at least one anterior fracture into a reduced position.

3. The method of claim 2, wherein the first and second receiver heads are manipulated prior to manipulating the first and second rods.

4. The method of claim 1, wherein manipulating the first and second receiver heads relative to the first and second rods comprises slidably moving the first and second receiver heads along the first and second rods.

5. The method of claim 1, wherein manipulating the first and second rods relative to an articulating joint comprises pivoting the first and second rods about the articulating joint to adjust an angle between the first and second rods.

6. The method of claim 1, wherein the first and second receiver heads are polyaxially coupled to the first and second bone screws such that the first and second receiver heads pivot relative to the first and second bone screws during at least one of positioning the first and second rods within the first and second receiver heads and manipulating the first and second receiver heads.

7. The method of claim 1, wherein the first and second receiver heads are locked to the first and second rods prior to locking the articulating joint.

8. The method of claim 1, further comprising coupling each of the first and second rods to at least one additional receiver head of at least one additional bone screw implanted in at least one additional vertebra.

9. The method of claim 8, wherein each of the first and second rods includes a proximal portion that is seated within the first and second receiver heads, respectively, and a distal portion that extends at an angle relative to the proximal portion and that is seated in the at least one additional receiver head, and wherein the proximal portion of each of the first and second rods extends in a medial-lateral direction relative to the vertebra, and the distal portion of each of the first and second rods extends in a craneal-caudal direction relative to the vertebra.

10. A method for reducing and stabilizing fractures in a vertebra, comprising:
   manipulating first and second receiver heads polyaxially coupled to first and second bone screws implanted in opposed first and second posterior-lateral sides of a vertebra to slide the first and second receiver heads along first and second rods seated within the receiver heads, thereby moving at least one posterior fracture in the vertebra into a reduced position;
   locking the first and second receiver heads relative to the first and second rods to maintain the at least one posterior fracture in the reduced position;
   manipulating the first and second rods to cause the first and second rods to pivot about a pivot joint coupling the first and second rods to thereby move at least one anterior fracture in the vertebra into a reduced position; and
   locking the pivot joint to maintain the at least one anterior fracture in the reduced position.

11. The method of claim 10, wherein the at least one posterior fracture comprises a first posterior-lateral fracture on a first posterior side of the vertebra and a second posterior-lateral fracture on a second posterior side of the vertebra, and the at least one anterior fracture comprises a first anterior-lateral fracture on a first anterior side of the vertebra and a second anterior-lateral fracture on a second anterior side of the vertebra.

12. The method of claim 10, wherein the articulating joint is positioned adjacent the spinous process between the first and second posterior-lateral sides of the vertebra.

13. The method of claim 10, wherein the articulating joint articulates in a posterior-anterior direction.

14. The method of claim 10, wherein the first and second receiver heads are manipulated and locked prior to manipulating the first and second rods.

15. The method of claim 10, wherein the first and second receiver heads pivot relative to the first and second bone screws when manipulating the first and second receiver heads.

16. The method of claim 10, further comprising coupling each of the first and second rods to at least one additional receiver head of at least one additional bone screw implanted in at least one additional vertebra.

17. The method of claim 16, wherein each of the first and second rods includes a proximal portion that is seated within the first and second receiver heads, respectively, and a distal portion that extends at an angle relative to the proximal portion and that is seated in the at least one additional receiver head, and wherein the proximal portion of each of the first and second rods extends in a medial-lateral direction relative to the vertebra, and the distal portion of each of the first and second rods extends in a craneal-caudal direction relative to the vertebra.

* * * * *